(12) United States Patent  (10) Patent No.: US 7,916,922 B2
Atzinger et al.  (45) Date of Patent: Mar. 29, 2011

(54) X-RAY IMAGE ORIENTATION IN RADIOGRAPHY AND FLUOROSCOPY

(75) Inventors: Franz Atzinger, Nürnberg (DE); Clemens Jörger, Forchheim (DE); Amy G. Schol, Dormitz (DE)

(73) Assignee: Siemens Aktiengesellschaft, Munich (DE)

( * ) Notice: Subject to any disclaimer, the term of this patent is extended or adjusted under 35 U.S.C. 154(b) by 887 days.

(21) Appl. No.: 11/843,775

(22) Filed: Aug. 23, 2007

(65) Prior Publication Data

US 2009/0052761 A1 Feb. 26, 2009

(51) Int. Cl.
*G06K 9/00* (2006.01)
(52) U.S. Cl. ...................................................... 382/132
(58) Field of Classification Search .......... 382/131–132; 378/4–42
See application file for complete search history.

(56) References Cited

U.S. PATENT DOCUMENTS 6,227,667 B1 * 5/2001 Halldorsson et al. ......... 351/206

* cited by examiner

*Primary Examiner* — Brian Q Le
(74) *Attorney, Agent, or Firm* — Schiff Hardin LLP

(57) ABSTRACT

In a method, apparatus, and computer program encoded with a data structure, for processing radiographic images and digital fluoroscopy radiographic (DFR) images acquired with the same imaging system using a single detector, three different types of image orientation are defined. These are a "system flip/rotation" that is dependent on the imaging system, a "pre-flip/rotation" orientation that is applied before the images are shown on a monitor, and a "post-flip/rotation" that is applied after an image is shown on the monitor. For this orientation change, the original image must be stored and subsequently manipulated. For pre-processing, DFR images are subjected only to the system flip/rotation, whereas radiographic images are subjected to the system flip/rotation as well as the pre-flip/rotation. For post-processing, both the DFR images and the radiographic images are subjected to the post-flip/rotation.

3 Claims, 2 Drawing Sheets

X-RAY IMAGE ORIENTATION IN RADIOGRAPHY AND FLUOROSCOPY

BACKGROUND OF THE INVENTION

1. Field of the Invention

The present invention concerns the presentation of medical images at a display, and in particular concerns a method and an apparatus for displaying radiographic and digital fluoroscopy radiographic images automatically with a correct orientation.

2. Description of the Prior Art

Historically in the field of x-ray diagnostics, two techniques have developed. In conventional radiography, a single exposure of a bone structure or the thorax, or some other radiation-attenuating anatomical structure is obtained. The other basic technique is fluoroscopy, wherein a series of images is acquired in real time. Dynamic processes such as gastrointestinal movements can be observed and diagnosed with fluoroscopy.

In an x-ray examination, it is known to employ orientation labels in order to identify the position of the patient in the x-ray exposure that is obtained, because many times the position of the patient during the actual radiation exposure cannot be discerned by viewing the subsequently developed image. Such labels can include side labels (R, L), labels that indicate the direction of the radiation through the patient (AP, PA) or identifiers indicating a rotation or an axis mirroring (flip) of the image.

When a diagnostician (radiologist) is using the exposure for diagnostic purposes, It is important that every change in the orientation of the image that has occurred up to the time that the radiologist used the image must be known to the radiologist, in order to enable an accurate diagnosis. Radiography exposures, however, are generally acquired by radiation technologists (RTs), and are only subsequently diagnosed by a radiologist.

By contrast, in digital fluoroscopy radiography (DFR), the radiologist conducts the examination and makes a diagnosis during or contemporaneously with the examination. During a DFR examination, it is desired to have an optimally good view of the patient by changing the image orientation on the monitor. Therefore, it is desired that only an image re-orientation that occurs in post-processing be displayed. This need for different types of orientation information depending on whether a radiographic examination or a DFR examination has been undertaken has not been of significant consequence in the past, because respectively separate systems were used to generate radiographic images and to generate DFR images. Recently, however, dual mode imaging systems have been developed that allow the same system to be operated in a radiographic imaging mode and in a DFR imaging mode. When these images are supplied to a pre-processing or post-processing computer, they both appear to be arriving from the same source (i.e., the image data acquisition system), and therefore it is a problem to accurately identify the different orientations and reorientations that have occurred in the case of radiographic images compared to the case of DFR images.

In analog radiography, for example, lead letters have been used for position detection, which are placed on the x-ray film and thus are visible in the image. Instead of a film, however, a digital detector is used in digital radiography, but the identification principle is similar. Generally, identification during the actual examination is not necessary in DFR, for the reasons discussed above. Only stored images that are viewed after the actual examination, and have been modified in terms of their orientation, must be identified in terms of orientation. The "output orientation" for the image is the orientation that existed at the time of the image acquisition.

SUMMARY OF THE INVENTION

It is an object of the present invention to provide a method and image viewing system that allow both radiographic and DFR images to be supplied thereto from the same image acquisition unit, and displayed with the proper orientation information. This object is achieved in accordance with the present invention by a method and apparatus wherein the raw x-ray image (radiographic image or DFR image) is acquired from a detector, and is processed with appropriate image processing steps for graphical display on a monitor with correct historical information indicating all image orientations and/or reorientations that have occurred.

With regard to orientation, the processing functions that are available are horizontal mirroring and/or vertical mirroring (flip) and rotation by 90° (ROT).

In accordance with the invention, three different types of orientation change are defined. The orientation change designated herein as "system flip/ROT" is a change in orientation based on the present system arrangement and the readout direction of the detector. This is necessary because for each examination designated setup-files (so called organ programs) are created. Organ programs shall not be changed due to a different system or detector arrangement.

This is set in a fixed manner due to the device configuration and depends, for example, on the installation direction of the detector. If the same detector is used for radiography and DFR, this setting is the same for both.

The orientation change defined herein as "pre-flip/ROT" is a change that is applied to the orientation before the image is shown on the monitor. This orientation thus occurs during the x-ray data acquisition.

The orientation change designated herein as "post-flip/ROT" is applied after the image is shown on the monitor, and thus occurs after the x-ray data acquisition. For this orientation change, the original image must be stored and subsequently manipulated.

Moreover, in accordance with the invention, the data flow is divided into two basic divisions, namely pre-processing (that occurs during the data acquisition) and post-processing (that occurs after the data acquisition).

DESCRIPTION OF THE PREFERRED EMBODIMENTS

Figure 1:
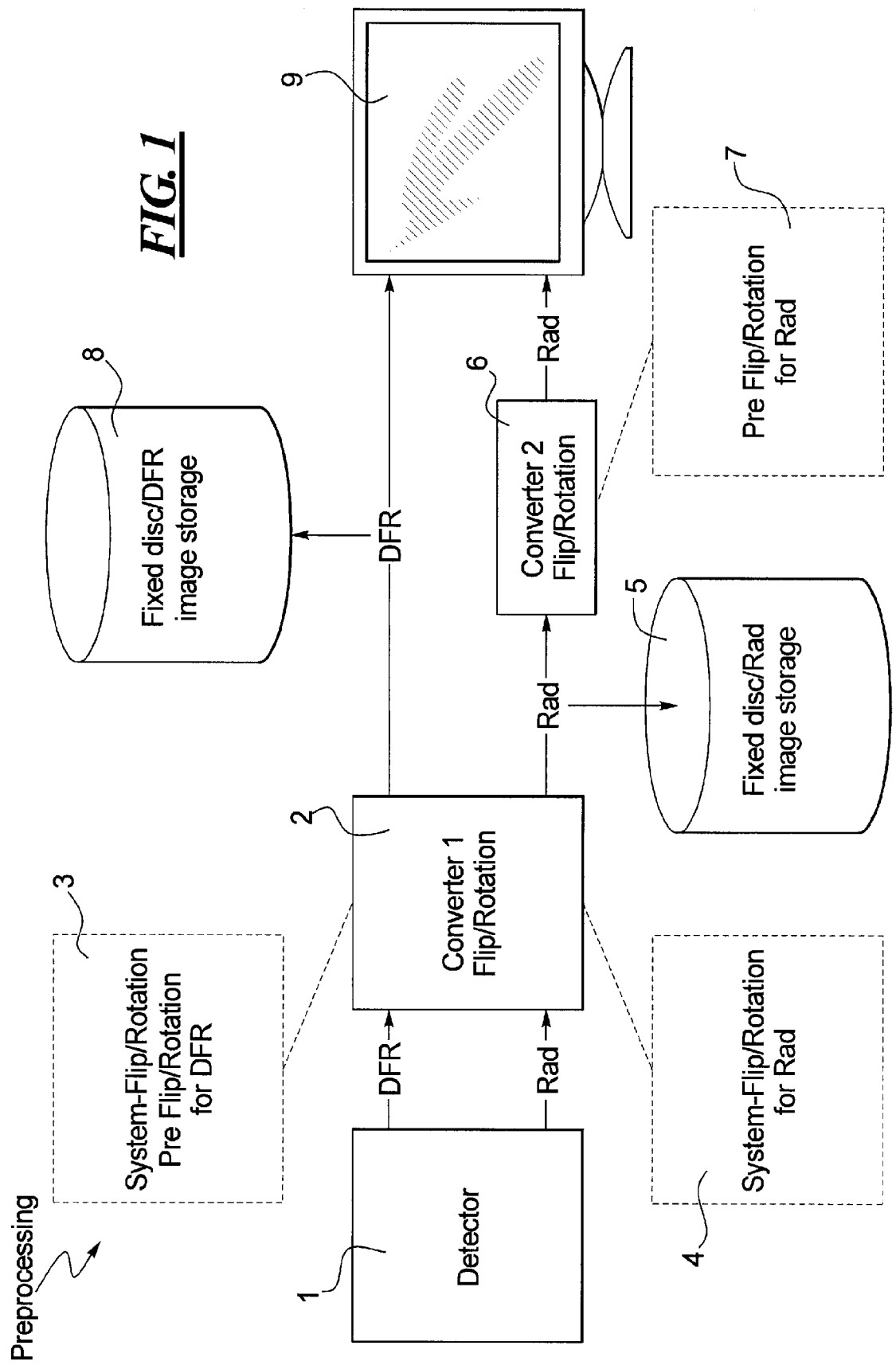
FIG. 1 schematically illustrates the components employed and the method steps that take place during pre-processing.

In the pre-processing procedure schematically illustrated in FIG. 1, DFR images (indicated DFR) and radiographic images (indicated Rad) both originate from the same detector 1. In accordance with the invention, both images are initially supplied to a converter 2 wherein flip/rotation occurs, designated converter A flip/rotation. As indicated in FIG. 1, the DFR images proceed directly from the converter 2 to a display 9. The Rad images, however, proceed to another converter 6, designated converter B flip/rotation. As schematically indicated by blocks 4 and 7, respectively, for the Rad images, a system flip/rotation occurs in the converter 2 and a pre-flip/rotation occurs in the converter 6. For DFR images, only the system flip/rotation occurs, in the converter 2. At the radiographic output of the converter 2, the flipped and rotated radiographic images may be stored in a fixed image storage 5, such as a disk storage. A fixed storage 8 is also connected to the DFR output of the converter 2.

In accordance with the invention, the DFR output of the converter 2 proceeds directly to the display 9. The Rad images, however, proceed to proceed to the display 9 only after the pre-flip/rotation for the Rad images takes place.

Figure 2:
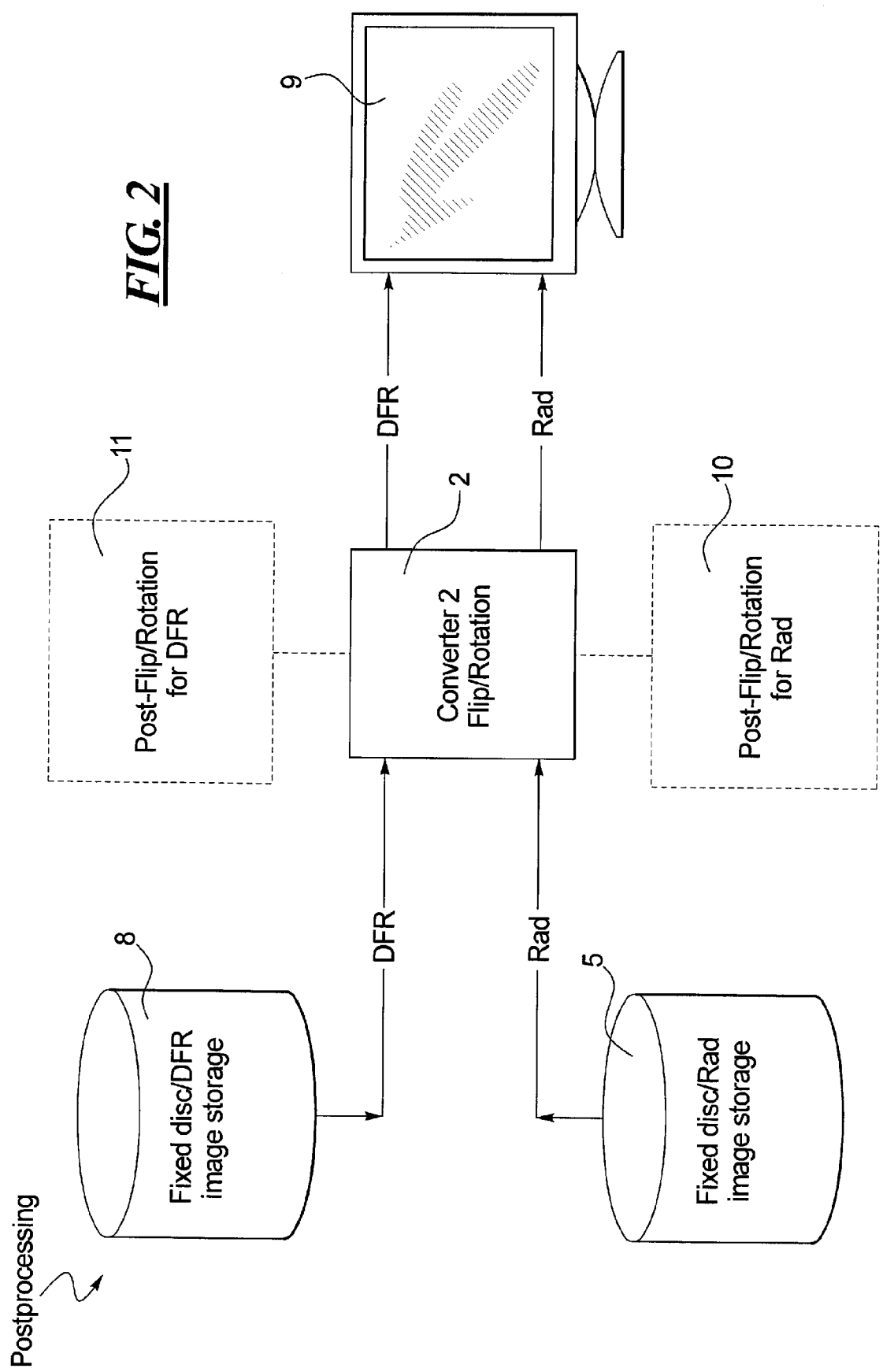
FIG. 2 schematically illustrates the components employed and the method steps that take place during post-processing.

As shown in FIG. 2, for post-processing, the DFR and Rad images are retrieved from their respective fixed storages 8 and 5, and are oriented (post-flip rotation 10 for Rad and post-flip rotation 11 for DFR) in the converter 6 and are subsequently shown at the display 9. The flow for both types of images is thus identical. The difference between DFR and radiography thus lies only in the pre-processing. For radiography, there is no difference between the pre-flip/ROT and the post-flip/ROT. This corresponds to the desired behavior, in which a radiographic image must retain its absolute (original) orientation both pre-flip and post-flip. In radiography, therefore, the image can always be returned again to the initial state, which is not possible, nor necessary, in DFR.

In accordance with the invention, therefore, the principles of image orientation for the user (viewer) are achieved in a single image system that is used for processing both radiographic and DFR images. Both the requirements for radiography and for DFR are taken into account in this single image processing system. Both the radiographic and DFR client, therefore, can retain their respective customary workflows, but in a combined radiographic/DFR system. In total, three orientations are differentiated (system-flip/ROT, pre-flip/ROT and post-flip/ROT), and these are achieved in two separate converters.

System-dependent reorientation, or some otherwise required reorientation, of the images (for example, due to different installation types of the detector) can be taken into account with a system-flip/rotation. This applies both for radiography and for DFR.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for processing and presenting radiographic and digital fluoroscopy radiographic (DFR) images comprising:

operating an imaging system that is capable of generating radiographic images and DFR images with a single radiation detector to obtain, at respectively different times, radiographic images and DFR images;

pre-processing said DFR images by supplying said DFR images to a first converter connected to said detector and automatically subjecting said DFR images to a system flip/rotation in said first converter to obtain pre-processed DFR images, and electronically storing said pre-processed DFR images;

visually presenting said pre-processed DFR images at a display;

pre-processing said radiographic images by supplying said radiographic images to said first converter and automatically subjecting said radiographic images to said system flip/rotation in said first converter to obtain initial pre-processed radiographic images, electronically storing said initial pre-processed radiographic images, and also supplying said initial pre-processed radiographic images from said first converter to a second converter and automatically subjecting said initial pre-processed radiographic images to a pre-flip/rotation in said second converter to obtain final pre-processed radiographic images;

visually presenting said final pre-processed radiographic images at said display;

after visually presenting said pre-processed DFR images at said display, post-processing said DFR images by supplying the electronically stored pre-processed DFR images to said second converter and automatically subjecting said pre-processed DFR images to a post-flip rotation in said second converter to obtain post-processed DFR images;

visually presenting said post-processed DFR images at said display;

after visually presenting said pre-processed radiographic images at said display, post-processing said radiographic images by supplying the electronically stored initial pre-processed radiographic images to said second converter and automatically subjecting said initial pre-processed radiographic images to said post-flip rotation in said second converter to obtain post-processed radiographic images; and visually presenting said post-processed radiographic images at said display.

2. A system for obtaining, processing and presenting radiographic and digital fluoroscopy radiographic (DFR) images comprising:

an imaging system that is capable of generating radiographic images and DFR images with a single radiation detector to obtain, at respectively different times, radiographic images and DFR images;

a first converter connected to said detector to which said DFR images are supplied for pre-processing, said first converter automatically subjecting said DFR images to a system flip/rotation to obtain pre-processed DFR images;

a storage in which said pre-processed DFR images are electronically stored;

a display at which said pre-processed DFR images are visually presented;

said radiographic images also being supplied from said detector to said first converter for pre-processing, said first converter automatically subjecting said radiographic images to said system flip/rotation to obtain initial pre-processed radiographic images, said initial pre-processed radiographic images also being electronically stored in said storage;

a second converter connected to said first converter, said initial pre-processed radiographic images being supplied from said first converter to said second converter and said second converter automatically subjecting said initial pre-processed radiographic images to a pre-flip/rotation to obtain final pre-processed radiographic images;

said final pre-processed radiographic images being visually presented at said display;

after visually presenting said pre-processed DFR images at said display, said second converter post-processing said DFR images by retrieving the electronically stored pre-processed DFR images and automatically subjecting said pre-processed DFR images to a post-flip rotation in said second converter to obtain post-processed DFR images;

said post-processed DFR images being visually presented at said display;

after visually presenting said pre-processed radiographic images at said display, said second converter also post-processing said radiographic images by retrieving the electronically stored initial pre-processed radiographic images and automatically subjecting said initial pre-processed radiographic images to said post-flip rotation in said second converter to obtain post-processed radiographic images; and said post-processed radiographic images being visually presented at said display.

3. A non-transitory computer-readable storage medium encoded with a data structure for processing and presenting radiographic and digital fluoroscopy radiographic (DFR) images obtained from an imaging system that is capable of generating radiographic images and DFR images with a single radiation detector at respectively different times, said data structure operating first and second converters to:

pre-process said DFR images by supplying said DFR images to said first converter connected to said detector and automatically subject said DFR images to a system flip/rotation in said first converter to obtain pre-processed DFR images, and electronically store said pre-processed DFR images;

visually present said pre-processed DFR images at a display;

pre-process said radiographic images by supplying said radiographic images to said first converter and automatically subject said radiographic images to said system flip/rotation in said first converter to obtain initial pre-processed radiographic images, electronically store said initial pre-processed radiographic images, and to also supply said initial pre-processed radiographic images from said first converter to said second converter and automatically subject said initial pre-processed radiographic images to a pre-flip/rotation in said second converter to obtain final pre-processed radiographic images;

visually present said final pre-processed radiographic images at said display;

after visually presenting said pre-processed DFR images at said display, post-process said DFR images by supplying the electronically stored pre-processed DFR images to said second converter and automatically subjecting said pre-processed DFR images to a post-flip rotation in said second converter to obtain post-processed DFR images;

visually present said post-processed DFR images at said display;

after visually presenting said pre-processed radiographic images at said display, post-process said radiographic images by supplying the electronically stored initial pre-processed radiographic images to said second converter and automatically subject said initial pre-processed radiographic images to said post-flip rotation in said second converter to obtain post-processed radiographic images; and visually present said post-processed radiographic images at said display.

* * * * *